(12) United States Patent
Augier et al.

(10) Patent No.: US 8,349,182 B2
(45) Date of Patent: Jan. 8, 2013

(54) FLUID DISTRIBUTION AND COLLECTION SYSTEM IN A MULTISTAGE COLUMN COMPRISING A JET BREAKER

(75) Inventors: Frederic Augier, Saint Symphorien D Ozon (FR); Denis Darmancier, Vienne (FR)

(73) Assignee: IFP, Rueil-Malmaison Cedex (FR)

( * ) Notice: Subject to any disclaimer, the term of this patent is extended or adjusted under 35 U.S.C. 154(b) by 523 days.

(21) Appl. No.: 12/493,684

(22) Filed: Jun. 29, 2009

(65) Prior Publication Data

US 2009/0321359 A1 Dec. 31, 2009

(30) Foreign Application Priority Data

Jun. 27, 2008 (FR) ..................................... 08 03692

(51) Int. Cl.
B01D 15/18 (2006.01)

(52) U.S. Cl. ..................... 210/283; 210/198.3; 210/284; 210/285

(58) Field of Classification Search ............... 210/198.3, 210/283, 284, 285
See application file for complete search history.

(56) References Cited

U.S. PATENT DOCUMENTS

| | | | |
|---|---|---|---|
| 3,214,247 A * | 10/1965 | Broughton | .................... 422/607 |
| 4,378,292 A | 3/1983 | Haase | |
| 5,755,960 A | 5/1998 | Callebert et al. | |
| 5,846,411 A | 12/1998 | Harter et al. | |
| 5,972,214 A | 10/1999 | Callebert et al. | |
| 6,471,861 B1 | 10/2002 | Burgard et al. | |
| 7,314,551 B2 * | 1/2008 | Frey et al. | .................. 210/198.2 |

FOREIGN PATENT DOCUMENTS

| | | |
|---|---|---|
| FR | 2740054 A1 | 11/1995 |
| WO | 2006055222 A1 | 5/2006 |

OTHER PUBLICATIONS

International Search Report corresponding to FR 08/03692, dated Jan. 21, 2009.

\* cited by examiner

*Primary Examiner* — Tony G Soohoo

*Assistant Examiner* — Peter Keyworth

(74) *Attorney, Agent, or Firm* — Millen, White, Zelano & Branigan, P.C.

(57) ABSTRACT

The present invention concerns a fluid distributor in a multistage column, each plate P of the column being divided into a certain number of panels Pa, and each panel Pa being equipped with a distributor of the invention, said distributor comprising:

a) a solid jet breaker located substantially in the axis of the outlet opening of the collecting baffle of the panel Pa;

b) an intermediate perforated plate extending laterally beyond the jet breaker, with a degree of opening in the range 10% to 40%;

c) a distribution plate extending over the entire panel Pa, and with a degree of opening in the range 5% to 20%.

15 Claims, 4 Drawing Sheets

FLUID DISTRIBUTION AND COLLECTION SYSTEM IN A MULTISTAGE COLUMN COMPRISING A JET BREAKER

CROSS-REFERENCE TO RELATED APPLICATION

This application is related to a previously filed application (application Ser. No. 12/492,476) entitled "NOVEL DISTRIBUTION AND COLLECTION SYSTEM IN A MULTISTAGE COLUMN FOR EQUALIZING THE RESIDENCE TIME ON EACH STAGE", Frederic Augier, claiming priority of French application Ser. No. 08/03.692 filed Jun. 27, 2008.

FIELD OF THE INVENTION

The invention relates to a novel device for distributing and collecting fluids in a multistage column employing a flow of said fluids in a solid particle medium termed a granular medium.

The term "multistage column" is applied to a column constituted by a plurality of plates disposed along a substantially vertical axis, each plate (termed the support plate) supporting a bed of granular solid, and the various successive beds being traversed in series by the fluid or fluids employed in the column. The fluid passing through the successive beds is termed the principal fluid in order to distinguish it from other fluids, termed secondary fluids, which may be added to the principal fluid via a distribution device generally located between two successive beds and termed distributor plates.

The present invention does not pertain to the system allowing injection of secondary fluids and for mixing said secondary fluids with the principal fluid, but solely to the distributor which is intended to distribute the fluid resulting from mixing the principal fluid and the secondary fluids over the granular bed located immediately downstream. The remainder of the text will refer simply to the "downstream" bed to designate the granular bed located immediately downstream of the distributor of the present invention.

The present invention thus concerns the distribution device which can supply each granular bed or at least a part thereof from a fluid which is in the form of a jet coming from the system for mixing the principal fluid and the secondary fluids equipping the preceding granular bed, i.e. more precisely the "upstream" bed in the sense of the direction of flow of the principal fluid.

In the remainder of the text, the term "variable resistance distribution device" (abbreviated to VRD) will be used to denote the principle of the distributor of the present invention.

More particularly, the invention pertains to the configuration of this distributor.

Each plate of the column has a plurality of VRD distributors linked in the manner in which the plate is divided into a plurality of sectors.

In general, each sector of the plate comprises one VRD distributor.

The invention essentially consists in that the distributor associated with each sector of a plate of row P comprises, in the direction of the principal flow:
 a solid jet breaker below the outlet from the collecting baffle, at a distance therefrom in the range 7 to 25 mm;
 an intermediate perforated plate with a width extending beyond the jet breaker;
 a distribution plate extending over the entire surface of the panel under consideration.

The invention means that plug type flow in the downstream bed of particles can be approximated, thereby optimizing the performance of the various processes carried out in multistage columns, such as simulated moving bed adsorption, for example.

The invention can also reduce the phenomenon of furrow formation at right angles to the jet leaving the mixing chamber; such furrows perturb to a greater or lesser extent the flatness of the upper surface of the granular bed located immediately downstream of the device under consideration.

The device of the present invention is thus assessed in the face of two criteria: the quality of the flow and the lack of formation of furrows at the upper surface of the downstream granular bed.

EXAMINATION OF THE PRIOR ART

Many devices are known for distributing, mixing or collecting a fluid in a vessel containing solid particles, in particular a multistage column. The distribution/mixing devices generally act to distribute a fluid as homogeneously as possible over the section of the column, to mix effectively the principal fluid passing through the various beds of the column with one or more secondary fluids introduced into each bed, and possibly to collect a flow of fluid between two beds, and finally to homogenize as far as possible the concentrations at the outlet from the bed before entering the next bed of solid particles, i.e. located immediately downstream of the device under consideration.

Further, the distribution/mixing devices must satisfy a certain number of constraints such as generating as little axial dispersion as possible, generating the minimum pressure drop, and not producing hydrodynamic perturbations which could alter the performance of the process.

Patents EP-0 074 815, US-2006/0108274 A1, FR-2 708 480 supply examples of distribution/mixing devices used in the case of simulated moving bed adsorption (SMB).

The distribution/mixing devices have a certain number of characteristics which are known to the skilled person. For clarity, reference will be made to the plate P and plate P+1 to designate the plate located immediately downstream in the direction of flow of the principal fluid:
 the plate P of the column is divided into regions or panels, which may have a variety of shapes, most usually being divided into angular sectors or into meridional panels, i.e. parallel panels which are substantially of the same length;
 in each panel of plate P, the principal fluid is collected via a "collecting baffle" system;
 the principal fluid leaving the granular bed is mixed with the secondary fluid which may be injected into the panel under consideration via a distribution network, terminating in an injection chamber;
 the mixture of the collected principal fluid and injected secondary fluid is re-distributed over the section of the panel of the next plate P+1 via a distribution device (screen, perforated plate or other) termed the distributor.

The fluid leaving the distributor then enters the bed of solid particles of bed P+1.

The bed of particles may be obturated by the distributor, i.e. there is no empty space between the distributor and the bed of particles P+1.

In contrast, an empty space may exist between the distributor and the bed, as indicated n patent US-2006/0108274 A1, FIG. 3B, for example.

In the case in which there is an empty space between the distributor and the bed, as described in US-2006/0108274 A1, the distributor must be designed so that it does not generate local fluid velocities which are too high at the bed inlet, in order not to cause partial fluidization of the particle bed.

Such a phenomenon could have a negative effect on the performance of the process.

This phenomenon is described in detail in patent US-2006/0108274 A1. That patent describes a jet breaker plate positioned above the distributor, and under the open zones corresponding to the outlet of a jet of liquid, in order to limit the high velocities of said jet at the inlet to the downstream granular bed. However, this may not be sufficient to eliminate this phenomenon, hence the necessary recourse to other solutions.

In order to further reduce this phenomenon, the prior art proposes several types of solution:

- positioning downstream of the distribution screen an element of the screen or perforated plate type in order to limit the turbulence and the high velocities at the inlet to the bed of particles;
- increasing the number of panels and the opening of the collecting baffles in order to reduce the velocity at which fluid passes through the distribution/mixing device.

Further, it is well known to the skilled person that any device producing sufficient pressure drop can in principle homogenize the velocity profiles at the outlet from that device. For this reason, the choice of distribution screen may have an impact on the velocity profile for fluid entering the bed of solid particles located downstream. The fact of increasing the pressure drop at the distributor to a greater or lesser extent may thus limit the risk of hydrodynamic perturbations at the particle bed inlet. However, this solution is not ideal as the increase in the pressure drop over the entire surface of the panels may be undesirable for strength reasons, or because of deterioration of the hydrodynamics in the distribution/mixing device.

Further, the use of a distributor with a high pressure drop may be a potential source of fouling or even partially clogging the distribution/mixing device.

BRIEF DESCRIPTION OF THE INVENTION

Figure 1:
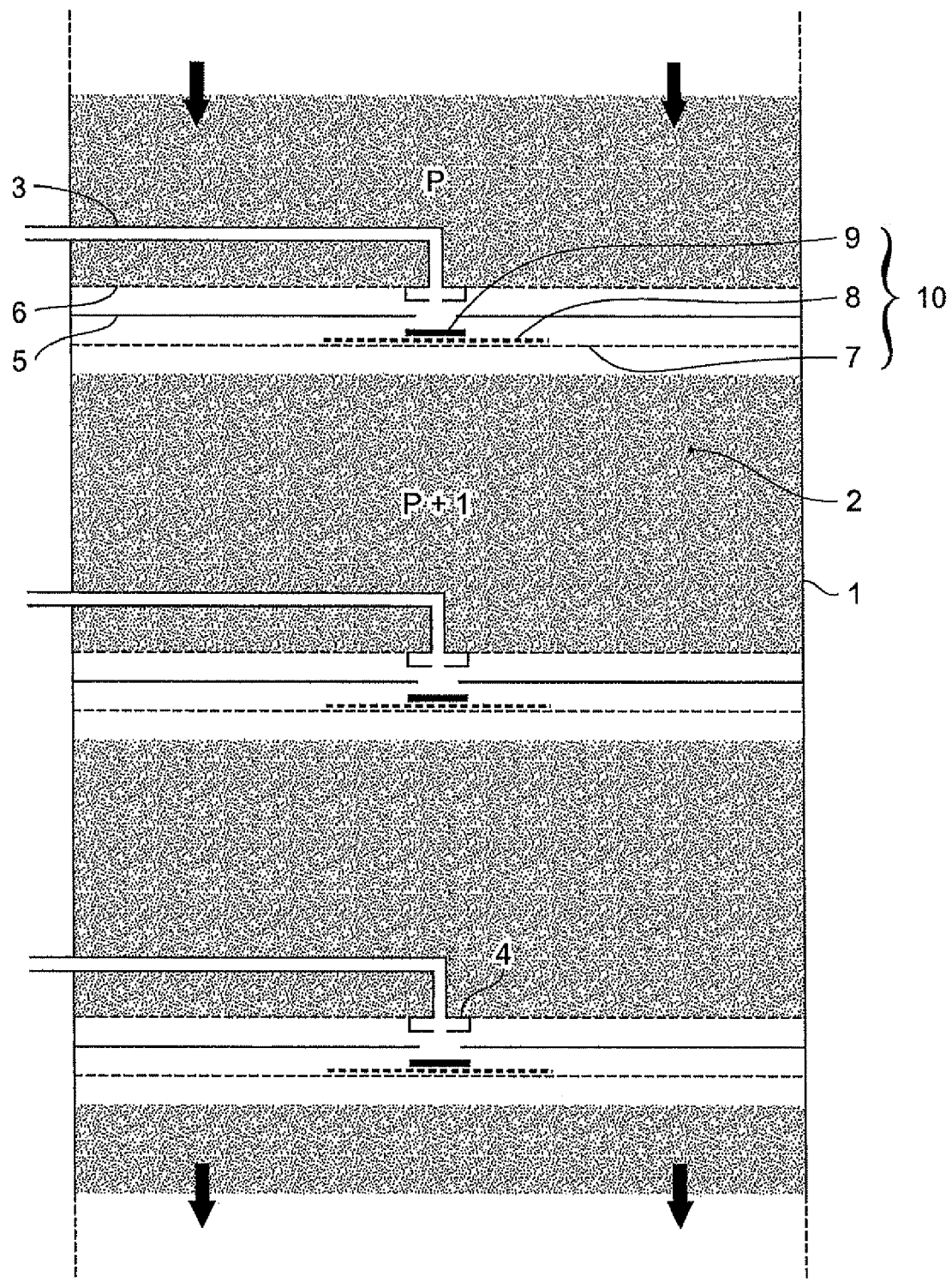
FIG. 1, in accordance with the invention, shows a multistage column with three successive plates, each plate being equipped with a system for collecting and injecting a secondary fluid and the distributor of the present invention.

The problem to be overcome by the present invention is that of improving the flow of fluids inside a column comprising a plurality of plates each carrying a bed of granular solid, termed a multistage column.

The term "improving the flow" as used in the present context means that the flow is as close to plug flow as possible (i.e. a flow in which the axial dispersion of fluid passing through the various successive beds of the column is as small as possible), and also that the phenomenon of furrow formation on the surface of the downstream granular bed is minimized or even dispensed with.

Overall, the column constitutes a granular medium and the principal fluid circulating between the various plates is a liquid in downflow mode.

The present invention consists of a distribution device which can supply a granular bed supported by a plate P, the upstream granular bed being supported by the plate P−1, having a system for collecting the principal fluid and for mixing said principal fluid with one or more secondary fluid(s) concluding in a baffle termed the collecting baffle having at least one outlet opening which generates a liquid jet with a velocity in the range 0.5 m/s to 4 m/s.

The principal fluid flows vertically downwardly.

More precisely, the present invention may be defined as a device for distributing a fluid supplying each granular bed of a multistage column having a succession of plates, each plate P supporting a bed of granular solid (sometimes denoted P for simplification), and being divided into panels denoted Pa, each panel Pa being equipped with a system for collecting fluid leaving said panel Pa essentially consisting of a baffle, termed the collecting baffle, having an outlet opening, said distribution device comprising the following three elements disposed from top to bottom in the direction of fluid flow:

a) a solid jet breaker located substantially in the axis of the outlet opening of the collecting baffle of the panel Pa;
b) an intermediate perforated plate extending laterally beyond the jet breaker, with a degree of opening in the range 10% to 40%, preferably in the range 15% to 30%;
c) a distribution plate extending over the whole of the panel Pa, and with a degree of opening in the range 5% to 20%, preferably in the range 7% to 15%.

In accordance with a preferred variation of the invention, the three elements constituting the distributor are disposed in the direction of fluid flow in the order:

a) the solid jet breaker;
b) the intermediate perforated plate;
c) the distribution plate.

The three elements are preferably adjoining in the sense that they are mutually juxtaposed. In certain cases, still within the scope of the invention, they may be separate from each other and in this case, the distance separating them is at most 10 mm, preferably at most 5 mm.

The term "distance" is defined as the distance separating the parts or ends which are closest of the two elements under consideration.

Dividing the plate into panels is known in the prior art. The two most usual types of division are division into meridional panels and division into panels corresponding to angular sectors. The meridional panels correspond to dividing the plate into parallel elements, orientated along a diameter of said plate, and having substantially the same width. The device of the present invention is compatible with any type of division of the plate into panels, more particularly division into meridional panels and into angular sectors.

In a variation of the invention, the fluid distribution device of the invention has a distribution plate which is a "Johnson" type screen, the slots of the "Johnson" screen being substantially perpendicular to the longitudinal (or meridional) axis of the panel. In accordance with another variation of the invention, the distribution plate is constituted by a simple perforated plate.

In another variation of the invention, the fluid distribution device has an intermediate plate which is a "Johnson" type screen, the slots of the "Johnson" screen being substantially perpendicular to the longitudinal axis of the panel.

In another variation of the invention, the intermediate plate is constituted by a plate perforated with holes with diameters in the range 0.5 mm to 1.5 mm.

In general, the intermediate plate extends over a width in the range between the width of the jet breaker and a value equal to half the length of the panel under consideration, plus or minus 5 cm.

Preferably, the width of the intermediate plate is in the range 10 to 30 cm.

In general, the jet breaker extends over a width in the range 2 to 6 cm, preferably in the range 3 cm to 5 cm.

In accordance with a variation of the invention, the distance included between the lower end of the collecting baffle of the panel Pa and the upper end of the jet breaker of panel Pa is in the range 4 mm to 30 mm, preferably in the range 7 mm to 25 mm.

The invention may also be described as a process for simulated moving bed separation using a device of the invention, in which the feed to be separated is any mixture of aromatic compounds containing 7 to 9 carbon atoms.

The invention may also be envisaged as a process for simulated moving bed separation using a device of the invention, in which the feed to be separated is a mixture of normal and iso-paraffins.

The invention may also be envisaged as a process for simulated moving bed separation using a device of the invention, in which the feed to be separated is a mixture of normal and iso-olefins.

The invention may also be viewed as a process for simulated moving bed separation using a device of the invention, in which the principal fluid passing through said device has a density in the range 600 to 950 kg/m$^3$ and a viscosity in the range 0.1 to 0.6×10$^{-3}$ Pa·s.

DETAILED DESCRIPTION OF THE INVENTION

The invention may be defined as a device for distributing a fluid deriving from an upstream collection system termed a collecting baffle, which has an opening for fluid to leave and which delivers said fluid in the form of a jet at a velocity in the range 0.5 to 4 m/s.

The distribution device of the invention can feed a granular bed located downstream of said device in a manner such that the flow of fluid is as close to plug flow as possible, and to minimize or prevent the formation of furrows on the upper surface of the downstream granular bed.

The device of the invention essentially comprises three elements:
- a) a solid jet breaker 9 located substantially in the axis of the outlet opening of the collecting baffle of the panel Pa−1;
- b) an intermediate perforated plate 8 extending laterally beyond the jet breaker, with a degree of opening in the range 10% to 40%, preferably in the range 15% to 30%;
- c) a distribution plate 7 extending over the entire panel Pa, and with a degree of opening in the range 5% to 20%, preferably in the range 7% to 15%.

The outlet opening of the collecting baffle of the panel Pa generally extends over the entire length of the panel under consideration.

The expression "substantially in the axis" of the outlet opening of the collecting baffle in paragraph a) means that the jet breaker is located below the outlet opening of the collecting baffle, centered about the median axis of said collecting baffle opening, and also extends over the entire length of the panel.

The term "laterally" used in paragraph b) means that the width of the intermediate perforated plate 8 is greater than that of the jet breaker 9 in the case of the meridional panel, the width being the dimension perpendicular to the longitudinal dimension of the meridional panel under consideration.

In the case of a panel with an angular sector shape, the term "laterally" means that the width of the intermediate perforated plate 8 is greater than that of the jet breaker 9, the width corresponding here to the radial dimension of the sector under consideration.

The remainder of the detailed description will be better understood using the accompanying figures.

FIG. 1 shows a column section constituted by 2 beds of solid particles denoted P for the upstream bed and P+1 for the downstream bed in the direction of flow of the principal fluid in said column.

Only two beds are shown, but the invention is also applicable to all of the constituent plates of the column including the first plate located at the inlet to the column.

The column is divided into a plurality of beds of solid particles 2 separated by a device for introducing one or more secondary fluids, termed the supply network 3, which terminates in an injection-extraction chamber 4 for injecting or withdrawing a quantity of fluid from the granular bed P.

An upper screen 6 or any other equivalent device supports the bed of particles P.

A collecting baffle 5 can recover the principal fluid flowing through the granular bed of the plate P.

The opening in the collecting baffle 5 is generally positioned such that the principal fluid coming from the upstream bed passes close to the opening or openings of the injection chamber 4.

The principal fluid which is collected thereby is mixed with the secondary fluid leaving the chamber 4.

The mixed principal and secondary fluids are re-distributed over the column section by passing through the distributor 10 which, in accordance with the invention, is constituted by 3 elements disposed in series in the direction of flow of the principal fluid:
- a) a jet breaker 9 located approximately in the axis of the collecting baffle 5;
- b) an intermediate plate 8 disposed beneath the jet breaker and extending laterally beyond said jet breaker, with a degree of opening in the range 10% to 40%, preferably in the range 15% to 30%;
- c) a distribution plate 7 located beneath the intermediate plate 8, extending over the entire panel Pa, and with a degree of opening in the range 5% to 20%, preferably in the range 7% to 15%.

One advantage of the device of the invention resides in the fact that below the openings in the collecting baffle 5 where high fluid velocities may exist, the intermediate perforated plate 8 can substantially reduce the velocity of the fluid passing through the distribution plate 7 while improving the distribution of said fluid over the downstream granular bed P+1.

Figure 2A:
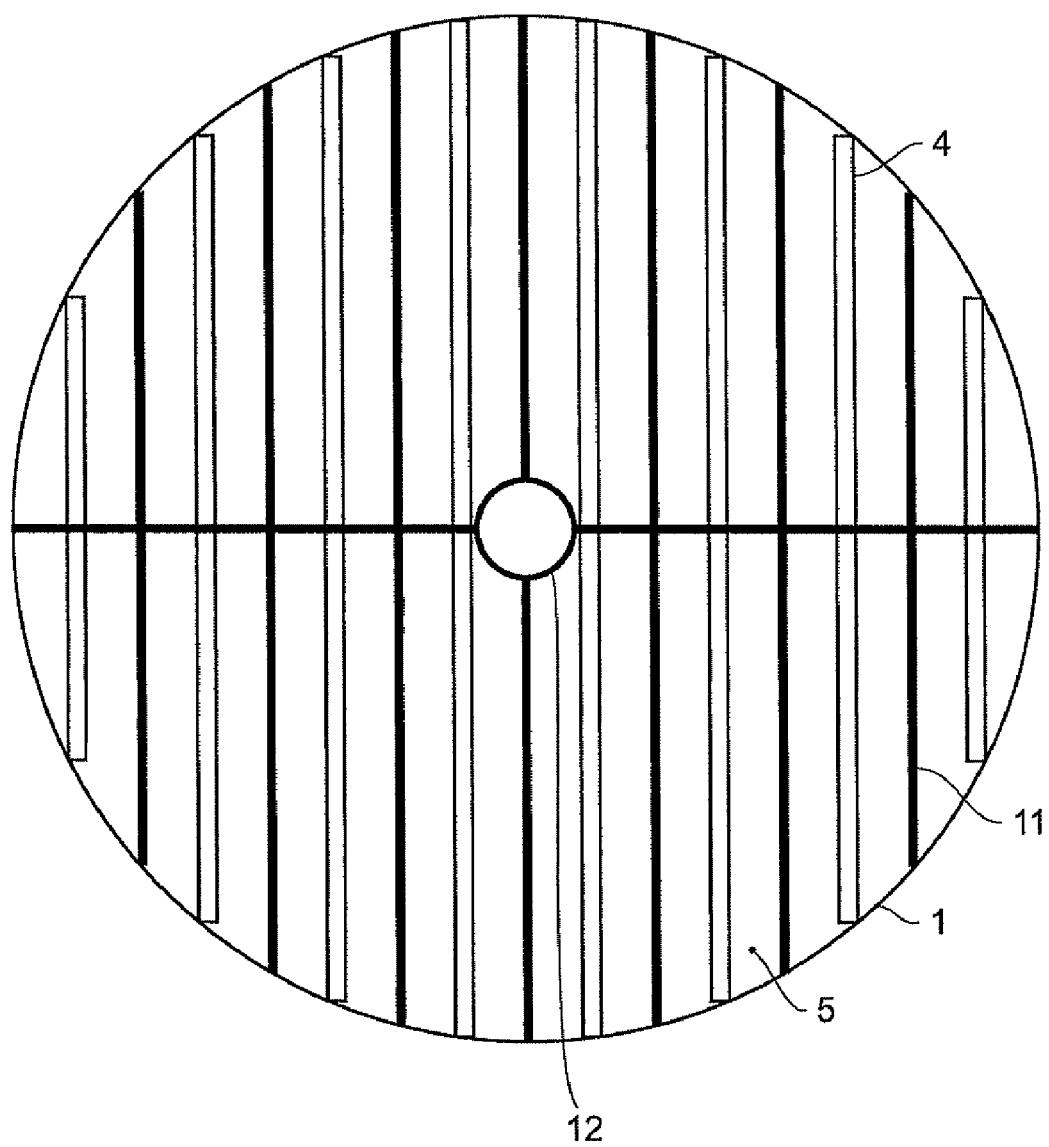
FIG. 2A, in accordance with the prior art, shows a top view of a plate divided into sectors termed meridional panels.

FIG. 2A, in accordance with the prior art, illustrates the support plate for the granular bed P divided into parallel meridional panels. Column 1 is divided into meridional panels 11.

The column in this case is equipped with a central support 12 which may act as a support point for the various panels or any beams supporting it.

FIG. 2A shows the injection-withdrawal chambers 4 and the collecting baffles 5. Each meridional panel 11 thus comprises an injection/withdrawal chamber 4 and a collecting baffle 5. It should be noted that the axis along which the panels of plate P are aligned may vary when moving to plate P+1. The invention is entirely compatible with any angle of offset between the panels of plate P and those of plate P+1.

Figure 2B:
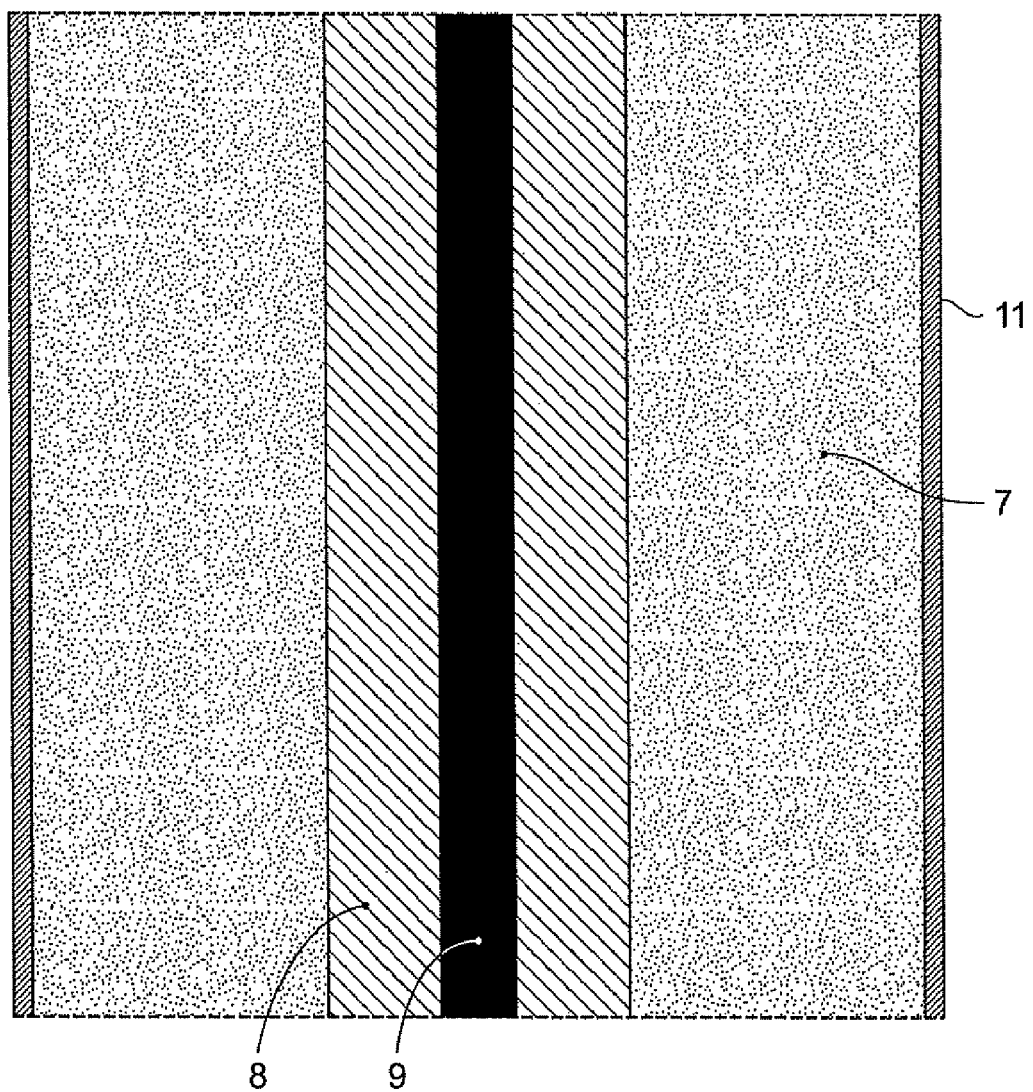
FIG. 2B, in accordance with the invention, shows a top view of a meridional panel and shows the extent of the jet breaker, the intermediate plate and the distribution plate.

FIG. 2B is a top view of a distributor of the invention applied to a meridional panel. The distributor 10 is composed of a distribution screen 7 covering the entire surface of the panel on which an intermediate perforated plate 8 and a jet breaker 9 are juxtaposed. The top view shows that in accordance with the invention, the intermediate perforated plate 8 extends laterally beyond the jet breaker 9. The term "laterally" in the context of the meridional panel means that extension of the intermediate screen 8 with respect to the jet breaker 9 is in the direction perpendicular to the longitudinal dimension of the panel under consideration.

Figure 3A:
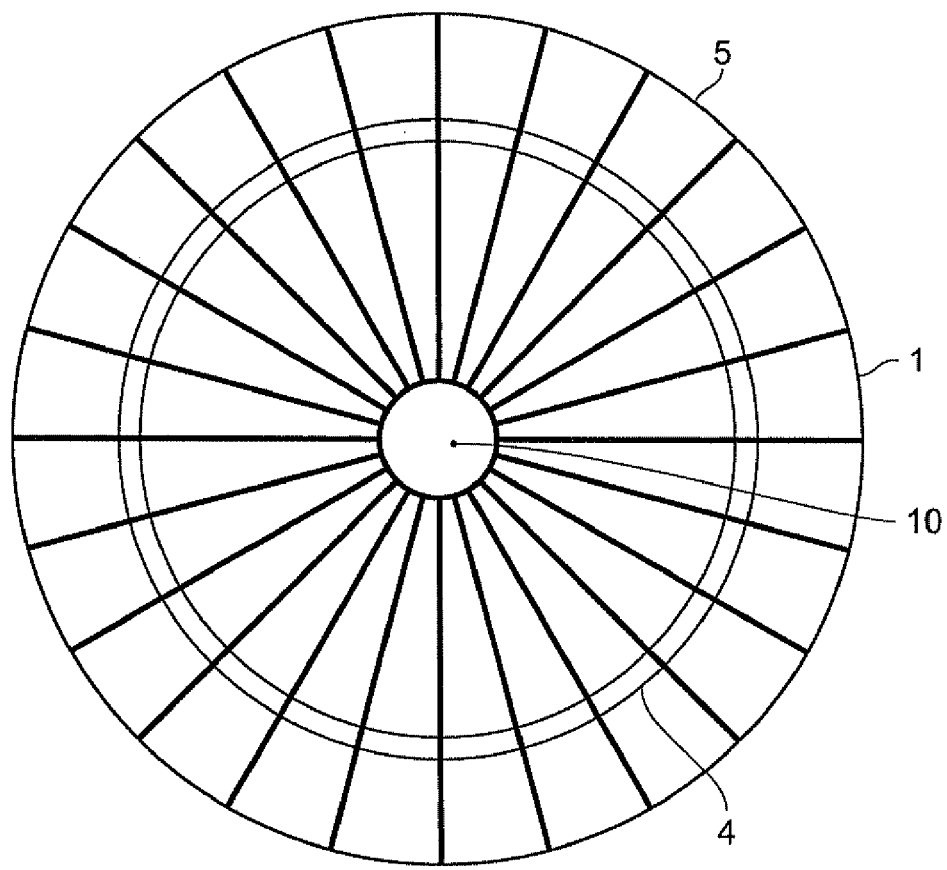
FIG. 3A, in accordance with the prior art, shows a top view of a plate divided into radial sectors.

FIG. 3A, in accordance with the prior art, illustrates the division of the plate formed into angular sectors.

Figure 3B:
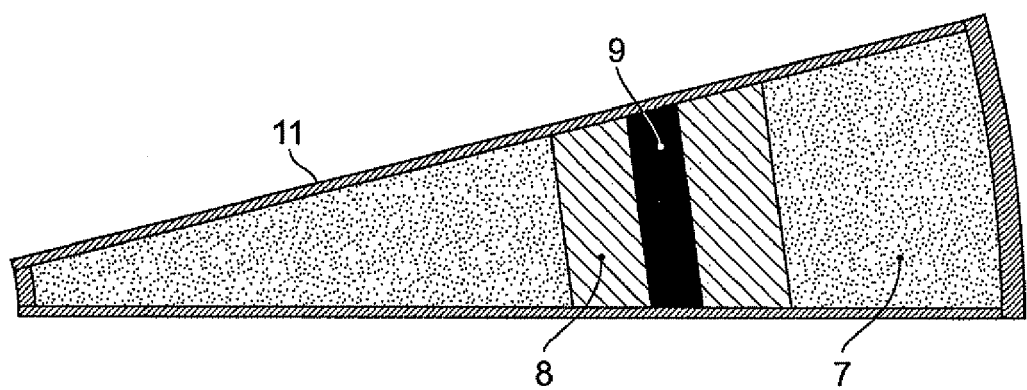
FIG. 3B, in accordance with the invention, shows a top view of a radial sector and shows the extent of the jet breaker, the intermediate plate and the distribution plate.

FIG. 3B is a top view of a distributor of the invention applied to a panel in the form of an angular sector.

In this case, the distributor 10 is composed of a distributor screen 7 covering the entire surface of the angular sector on which an intermediate perforated plate 8 and a jet breaker 9 have been juxtaposed. The top view shows that, in accordance with the invention, the intermediate perforated plate 8 extends laterally beyond the jet breaker 9.

The term "laterally" as used in the context of an angular sector panel means that the extension of the intermediate screen 8 with respect to the jet breaker 9 is in the radial direction of the panel under consideration.

EXAMPLE

The effectiveness of the device of the invention was tested using Plexiglass mock-ups.

The mock-up reproduced a portion of the bed and a device of the invention as shown in FIG. 1.

The plate was divided into meridional panels.

The width of the meridional panel was 1.2 m; the height of one bed was 1.2 m.

The depth of the mock-up was 18 cm. The collecting baffle 5 located below the granular bed P was perforated with holes 30 mm in diameter and with a 60 mm centre-to-centre-distance.

The mock-up was filled with a zeolite sieve with a granulometry centred about 610 µm.

The mock-up was filled to a height of 10 mm below the distributor of the invention.

The mock-up was supplied with water at a superficial velocity of 2 cm/s.

Several configurations of the distributors were tested and are recorded in Table 1.

The test distributors were composed of the following elements:
a) jet breaker 9 with various widths;
b) intermediate plates 8 perforated with 1 mm diameter holes with various degrees of opening and widths;
c) a distribution plate 7 constituted by a screen with various openings covering the whole mock-up.

All of the elements were centred below the opening of the collecting baffle 5.

In the event of perturbation of the bed of particles, a furrow was generally observed substantially directly below the opening of the collecting baffle 5. This furrow was the result of local fluidization of particles induced by the presence of high jet velocities at the outlet from the collecting baffle.

The furrow heights (max furrow) formed on the upper surface of the granular bed located downstream of the device were measured for each test and constituted a first parameter for assessing the performance of the distributors.

Secondly, the measurements for the residence time distribution (RTD) were carried out to quantify the axial dispersion in the bed supplied by the distributor under study. To this end, the mock-up was filled with 1 mm diameter glass beads in a manner analogous to filling with the zeolite beads, the glass beads being more suited to measuring the RTD.

The RTD method is explained in a number of works, including "Génie de la réaction chimique" [Chemical reaction engineering] by D Scweich, 2001, Tec&Doc, publishers, Paris.

The results are shown in the form of the Peclet number which expresses the ratio between fluid convection and axial dispersion. The higher the Peclet number, the smaller the axial dispersion.

Minimizing axial dispersion is generally beneficial to processes employing fixed beds of solid particles, in particular adsorption processes. Axial dispersion constitutes the second parameter for assessing the performance of the distributors.

TABLE 1

Summary of tests carried out

| Case | Jet breaker width | % screen | % perforated plate | Width perforated plate | Max furrow | Peclet |
|---|---|---|---|---|---|---|
| Case 1 | 0 | 12.0% | — | — | 5 cm | 280 |
| Case 2 | 4 cm | 12.0% | 20% | 20 cm | 0 | 370 |
| Case 3 | 4 cm | 12.0% | 3% | 20 cm | 2 cm | 308 |
| Case 4 | 4 cm | 12.0% | 10% | 20 cm | 1 cm | 310 |
| Case 5 | 4 cm | 12.0% | 30% | 20 cm | 0 | 350 |
| Case 6 | 4 cm | 12.0% | 20% | 12 cm | 1 cm | 322 |
| Case 7 | 4 cm | 12.0% | 20% | 30 cm | 0 | 368 |
| Case 8 | 4 cm | 12.0% | 20% | 60 cm | 0 | 340 |

Case 1 is in accordance with the prior art.

Case 1 did not have a jet breaker. It acted as a reference case, and its performance was observed to be poorer with a Peclet number of 280 and a furrow with a depth of 5 cm.

The best result was obtained with a distributor of the invention corresponding to case 2, composed of:
a) a jet breaker 9 which was 94 cm wide;
b) an intermediate plate 8 perforated with 1 mm holes, located below the jet breaker and centred on the axis of said jet breaker, which was 20 cm wide, and had a 20% opening;
c) a distribution screen 7 with a 12% opening extending over the entire section of the panel.

This distributor maximized the Peclet number (370) while eliminating the formation of furrows in the downstream granular bed.

Cases 3, 4 and 5 in accordance with the invention show optimization of the degree of opening of the intermediate perforated plate. An intermediate perforated plate opening of 3% (case 3) and 10% (case 4) produced inferior results to that of the intermediate plate with an opening of 30% (case 5).

Similarly, cases 6, 7 and 8 of the invention show that there is an optimized value for the width of the intermediate plate, this optimized value being close to 20 cm.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding FR application Ser. No. 08/03.692, filed Jun. 27, 2008, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A device comprising:
    A. at least one granular bed of a multistage column having a succession of support plates, each support plate (P) supporting a bed of granular solid and being divided into panels (Pa), wherein each panel is equipped with a collecting baffle that has an outlet opening, and
    B. a fluid distribution device comprising the following three elements disposed from top to bottom in the direction of fluid flow:
        a) a solid jet breaker (9) located approximately in the axis of the outlet opening of the collecting baffle of the panel (Pa) and centered on the axis of said collecting baffle;
        b) an intermediate perforated plate (8) extending laterally beyond the jet breaker over a width in the range from the width of said jet breaker to a higher value equal to half the width of the panel plus or minus 5 cm, and extending over less than the entire section of the panel (Pa), and with a degree of opening in the range 15% to 30%;
        c) a distribution plate (7) extending over the entire section of the panel (Pa), and with a degree of opening in the range 7% to 15%, and
    wherein said fluid distribution device is applied to each panel (Pa) of the support plate (P) equipped with the collecting baffle (5) located immediately upstream of the fluid distribution device.

2. The device of claim 1, wherein the three elements of the distribution device: the solid jet breaker (9), intermediate perforated plate (8) and distribution plate (7), adjoin one another.

3. The device of claim 2, wherein the panels (Pa) are of the meridional type corresponding to divisions of the support plate (P) into parallel elements orientated along a diameter of said support plate (P) and having substantially the same width.

4. The device of claim 3, wherein the distribution plate (7) is a "Johnson" type screen, the slots of the screen being substantially perpendicular to the longitudinal axis of the panel.

5. The device of claim 4 wherein the intermediate perforated plate (8) is a "Johnson" type screen, the slots of said screen being substantially perpendicular to the longitudinal axis of the panel.

6. The device of claim 1, wherein the three elements of the fluid distribution device: the solid jet breaker (9), intermediate perforated plate (8) and distribution plate (7), are separate from each other, the distance separating them being at most 10 mm.

7. The device of claim 6 wherein said distance separating the three elements of the fluid distribution device is at most 5 mm.

8. The device of claim 1, wherein the panels (Pa) are of the meridional type corresponding to divisions of the support plate (P) into parallel elements orientated along a diameter of said support plate (P) and having substantially the same width.

9. The device of claim 1, wherein the distribution plate (7) is a "Johnson" type screen, the slots of the screen being substantially perpendicular to the longitudinal axis of the panel.

10. The device of claim 9, wherein the intermediate perforated plate (8) is a "Johnson" type screen, the slots of said screen being substantially perpendicular to the longitudinal axis of the panel.

11. The device of claim 1, wherein the intermediate perforated plate (8) is a "Johnson" type screen, the slots of said screen being substantially perpendicular to the longitudinal axis of the panel.

12. The device of claim 1, wherein the solid jet breaker (9) extends over a length in the range of 2 cm to 6 cm.

13. The device of claim 12 wherein said solid jet breaker (9) length is in the range of 3 cm to 5 cm.

14. The device of claim 1, wherein the distance between the lower end of the collecting baffle (5) and the upper end of the jet breaker (9) is in the range of 4 mm to 30 mm.

15. The device of claim 14 wherein said distance between the lower end of the collecting baffle (5) and the upper end of the jet breaker (9) is in the range of 7 mm to 25 mm.

* * * * *